United States Patent
Eklund et al.

(10) Patent No.: US 7,814,776 B2
(45) Date of Patent: Oct. 19, 2010

(54) CARBON NANOTUBE-QUARTZ RESONATOR WITH FEMTOGRAM RESOLUTION

(75) Inventors: Peter C. Eklund, State College, PA (US); Abhijat Goyal, Tempe, AZ (US); Srinivas A. Tadigadapa, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 161 days.

(21) Appl. No.: 11/719,120

(22) PCT Filed: Nov. 10, 2005

(86) PCT No.: PCT/US2005/040833

§ 371 (c)(1),
(2), (4) Date: Dec. 9, 2008

(87) PCT Pub. No.: WO2006/112883

PCT Pub. Date: Oct. 26, 2006

(65) Prior Publication Data

US 2009/0145233 A1 Jun. 11, 2009

Related U.S. Application Data

(60) Provisional application No. 60/627,063, filed on Nov. 11, 2004, provisional application No. 60/627,239, filed on Nov. 12, 2004.

(51) Int. Cl.
*G01N 29/02* (2006.01)
(52) U.S. Cl. .................................................. 73/24.01
(58) Field of Classification Search ........................ None
See application file for complete search history.

(56) References Cited

U.S. PATENT DOCUMENTS

| | | | | |
|---|---|---|---|---|
| 6,997,039 | B2 * | 2/2006 | Rao et al. | 73/24.06 |
| 7,270,002 | B2 * | 9/2007 | Chen et al. | 73/335.02 |
| 7,452,452 | B2 * | 11/2008 | Ren et al. | 204/400 |
| 2004/0016287 | A1 * | 1/2004 | Fu | 73/23.34 |

FOREIGN PATENT DOCUMENTS

| | | |
|---|---|---|
| JP | 8-181562 | 7/1996 |
| WO | WO 03/091458 A1 | 11/2003 |

OTHER PUBLICATIONS

Dai, L. et al., "Sensors and sensor arrays based on conjugated polymers and carbon nanotubes", Pure & Appl. Chem., vol. 74, No. 9, pp. 1753-1772 (2002).

(Continued)

*Primary Examiner*—Robert R Raevis
(74) *Attorney, Agent, or Firm*—McKee, Voorhees & Sease, P.L.C.

(57) ABSTRACT

Methods for sensing and building sensors provide for adding nanotubes to a sensor to improve characteristics such as the Q-factor associated with the sensor. Mass loading and damping characteristics of micromachined quartz crystal resonators on which a thin film of debundled single-walled carbon nanotube (SWNT) has been deposited are disclosed. An absolute mass sensitivity of ~100 fg was experimentally measured by monitoring the continuous desorption of gases from SWNT surfaces in a vacuum ambient.

11 Claims, 5 Drawing Sheets

OTHER PUBLICATIONS

Goyal, A. et al. "Improvement in Q-factor of AT-cut Quartz Crystal Resonators using Single Walled Carbon Nanotubes", IEEE Ultrasonics Symposium, vol. 2, pp. 1167-1170 (2005), Abstract XP010899032.

Penza, M. et al., "Carbon nanotubes as SAW chemical sensors materials", Senors and Actuators B, Elsevier Sequoia S.A., vol. 100, pp. 47-59 (2004), Abstract XP004509048. Feb. 2004.

Penza, M. et al., "Acoustic and Optical Senors Incorporating Carbon Nanotubes for Detection of Organic Solvents", Sensors, Proceedings of IEEE Vienna, Austria, pp. 403-406, XP010793419 (2004).

Sumanasekera, G.U. et al., "Thermoelectric Chemical Sensor Based on Single Wall Carbon Nanotubes" Mol. Cryst. Liq. Cryst., vol. 387, pp. 31-37 (2002), Abstract XP 001183606.

Vig, J.R. et al., "Fundamental Limits on the Frequency Instabilities of Quartz Crystal Oscillators", IEEE International Frequency Control Symposium, pp. 506-523 (1994), Abstract XP010137826.

Ciplys, D. et al., "Attenuation of surface acoustic waves by carbon nanotubes", Surface Engineering 2002—Synthesis Characterization and Applications Symposium, vol. 750, pp. 211-216 (2002), Abstract XP 009073025.

* cited by examiner

CARBON NANOTUBE-QUARTZ RESONATOR WITH FEMTOGRAM RESOLUTION

PRIORITY STATEMENT

This application is a national stage entry of PCT/US05/40833 filed on Nov. 10, 2005 which claims the benefit of U.S. Provisional Application No. 60/627,239 filed on Nov. 12, 2004 and U.S. Provisional Application No. 60/627,063 filed on Nov. 11, 2004.

BACKGROUND OF THE INVENTION

The present invention relates to sensors. More particularly, but without limitation, the present invention relates to sensors having an increased quality factor.

The advent of high-density plasma sources and fluorine-based etch chemistries, as well as developments in wet etching techniques, with high anisotropy and surface smoothness, have made it possible to realize quartz crystal shear-mode resonators with thicknesses less than 30 µm and diameters down to 100 µm[1,2]. These resonators can be easily configured as high sensitivity mass sensors, and are known as a quartz crystal microbalance (QCM)[3]. Until now, the large size of the QCMs has limited their widespread use for bio(chemical) sensing. Planar arrays of these mass sensors can now be realized, and without the drawbacks associated with flexural components[4,5]. These micromachined QCM arrays promise to be a robust platform for future (bio)chemical sensors.

The concept of mass measurement quartz resonators was first presented by Sauerbrey who found that the frequency change Δf is related to the mass loading Δm by[6]

$$\Delta f = -(2f_0^2(0)/A\sqrt{\rho_q \mu_q})\Delta m, \quad (1)$$

where $f_0(0)$ is the unloaded resonant frequency, $\mu_q$ is the shear modulus, $\rho_q$ is the density, and A is the area of the electrode on the quartz crystal[7]. The minus sign indicates the resonance frequency decreases upon mass loading. The relation given by eq. (1) holds only when the thin adsorbed film is well anchored to the sensor surface and not subject to viscous losses. A micromachined 30 µm thick and 11 mm diameter resonator is expected to have a sensitivity of ~1 pg/Hz, a factor of ~20,000 improvement in absolute mass sensitivity in comparison to a commercially available 5 MHz device[3].

It is implicitly assumed that the high Q-factor of the resonators necessary to achieve high mass resolution is maintained to: achieve the improved mass sensitivity by miniaturization of the QCM. To this end, the energy loss mechanisms in the resonating quartz crystal need to be minimized, and the acoustic energy needs to be confined to within the active (electrode) area of the crystal. Due to the energy trapping effects, it been observed that the differential mass sensitivity of the QCM is a maximum at the center and decreases towards the edges of the electrode[8,9]. In fact, the simple proportionality found between the frequency shift and the deposited mass in eq. (1) is valid only if the material is homogeneously distributed over the crystal[10]. For example, on a 1 mm diameter resonator, a uniform gold film $7 \times 10^{-5}$ nm thickness needs to be uniformly deposited to observe the predicted sensitivity of 1 pg/Hz. Thus, in spite of all the advances in the miniaturization of the quartz resonators, direct mass calibration curves following the Sauerbrey equation (eq. 1) have been reported only for nanogram loadings[2]. From these calibration curves, extremely high sensitivities are typically projected, i.e., picograms or even femtograms. However, they have not actually been directly demonstrated.

BRIEF SUMMARY OF THE INVENTION

Therefore it is a primary object, feature, or advantage of the present invention to improve upon the state of the art.

It is another object, feature, or advantage of the present invention for increasing quality factor of a sensor.

It is another object, feature, or advantage of the present invention for increasing quality factor of resonators that can be used in sensors.

A further object, feature, or advantage of the present invention is to improve the characteristics of a sensor by adding a layer of nanotubes to the sensor.

One or more of these and/or other objects, features or advantages of the present invention will become apparent from the specification and claims that follow.

According to one aspect of the present invention, a method for increasing the quality factor of one or more sensors is disclosed. The method provides for adding a layer of nanotubes to at least one sensor to thereby increase the quality factor of the one or more sensors. The one or more sensors can be of various types, including, without limitation, conducting and non-conducting regions sensors, SAW sensors, Quartz Crystal, flexure mode mechanical structures, Microbalance sensors, conductive composite sensors, piezoelectric sensors, and sensors based on a cantilever or a bridge. The one or more sensors can be a resonator.

The present invention provides for numerous and diverse techniques that can be used for adding the nanotubes, including such techniques as spray on, spin on, vacuum deposition, and in situ growth. Where the one or more sensors comprise of a cantilever or a bridge, the present invention contemplates that the cantilever or bridge may be formed in numerous ways, including through micromachining, chemical vapor deposition, physical vapor deposition, and plasma enhanced deposition.

The one or more sensors may be a part of a sensing device that includes a housing that encloses the one or more sensors. The sensing device can include various circuitry, such as, without limitation, automatic gain controllers, amplitude controllers, phase controllers, temperature controllers, oscillators, input ports for subjecting the one or more sensors to an input signal, and output ports for reading a response of the one or more sensors. The circuitry may also be adapted to allow a computer to read the one or more sensors. Where the sensing device includes a housing, a preconcentrator may be operatively connected to the one or more sensors. The sensor may be portable or handheld. A sensor housing can be adapted to function as a radiation shield, an electromagnetic shield or used to control ambient temperature of the one or more sensors.

Where the one or more sensors is a quartz crystal microbalance sensor, the mass sensitivity of the quartz crystal microbalance sensor can be increased. Such an increase is achieved through micromachining in the form of a thin diaphragm of thickness ranging from 2 nm to 100 microns. The area of the electrodes is then reduced on at least one side of the diaphragm. The surface roughness of the micromachined diaphragm is then reduced. Edges of the diaphragm are then beveled to confine acoustic energy within the area defined by the electrodes. The opposing faces of the sensor are made non-parallel to each other.

The one or more sensors of the present invention can be integrated with thermopiles. The one or more sensors can be used a pressure sensor, mass sensor, or temperature sensor.

According to another aspect of the present invention the layer of nanotubes is a layer of carbon nanotubes. The layer of carbon nanotubes can be used as a functionalization layer. The functionalization layer is adapted for use in any number of applications, including, without limitation, chemical sensing, gas sensing applications, virus detection applications, DNA sequencing applications, artificial olfactory unit applications, hydrogen storage element applications, and biochemical applications.

According to another aspect of the present invention the nanotubes need not be carbon nanotubes but can be made of materials such as, but not limited to semiconductor materials, polymer materials, organic materials, and a combination of these types or other types of materials.

According to another aspect of the present invention, the overlayer need not be limited to nanotubes, but can be in the form of nanowires, thin films and other kinds of nano structures. Also, these can be made of materials such as, but not limited to semiconductor materials, polymer materials, organic materials, and a combination of these type and other type of materials.

According to another aspect of the invention the nanotubes are added to one or more faces of the at least one sensor. Where the nanotubes are added to one face of the sensor, another face can be coated with a functionalization layer. The functionalization layer can include, without limitation, a self-assembled monolayer or a polymer. The present invention also provides for adding nanotubes to one face and coating the other face with nanowires or nanofibers. The nanowires or nanofibers can be made of a number of types of materials, including, without limitation, polymers, semiconductors, and carbon.

According to another aspect of the present invention, the sensor can include electrodes. The electrodes may be made of any of a number of types of material including, but not limited to Au, Pt, Ti, Cr, and Ni.

According to another aspect of the present invention, the output from the sensor may be used in various ways. For example, the output from the sensor can be analyzed by comparing the output to one or more databases. The present invention also provides for modifying the output from the sensor with associated circuitry and then analyzing the modified output by comparing to a database.

The present invention also contemplates variations in the manner in which the sensor is formed. For example, the sensor may be formed on a single substrate or multiple substrates. Where multiple substrates are used, the multiple substrates can be functional elements of one or more sensors.

The present invention contemplates numerous variations in the application of the sensors. For example, one or more sensors may be adapted for use to detect binding between a first and a second member of a recognition pair, said recognition pair being a pair selected from the group consisting of antigen-antibody, ligand-receptor, sugar-lectin, biotin-avidin, enzyme-substrate, and oligonucleotide-oligonucleotide with a complimentary sequence, oligonucleotide-protein, and oligonucleotide-cell.

According to another aspect of the present invention, addition of a layer of nanotubes to one or more sensors controls frequency stability or quality factor for use of the one or more sensors as a frequency reference. The adding of the layer of nanotubes controls frequency stability or quality factor so that the one or more sensors can be used as a clock generator.

Where the one or more sensors is a resonator, the adding of a layer of nanotubes provides for tuning frequency of the resonator to a desired level. The adding of a layer of nanotubes to the one or more sensors also provides for increasing the frequency stability of the resonator.

According to another embodiment of the present invention a sensing device includes a substrate with one or more sensors disposed on the substrate. A layer of nanotubes is deposited on the sensor.

DETAILED DESCRIPTION OF THE PREFERRED EMBODIMENT

Figure 1A:
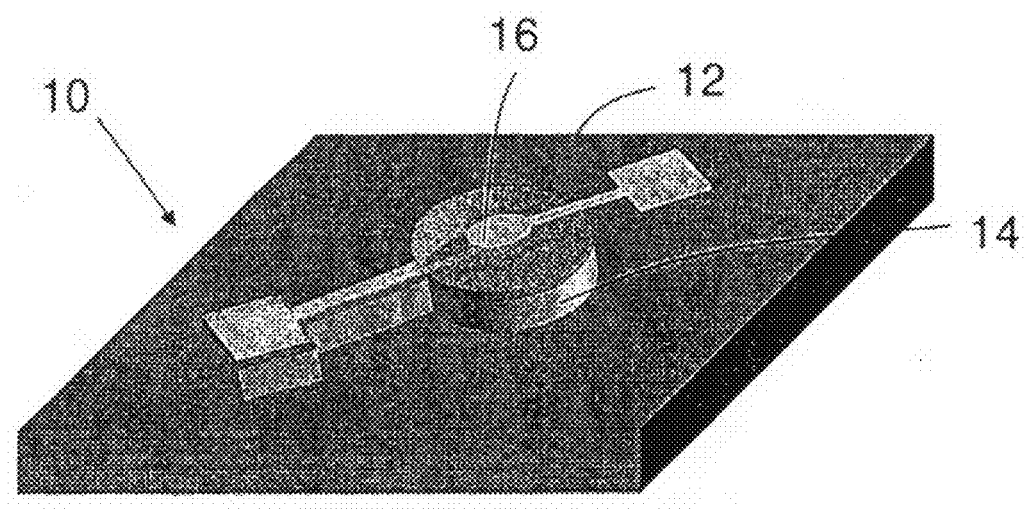
FIG. 1A is a schematic diagram of the micromachined quartz resonator.
Figure 1B:
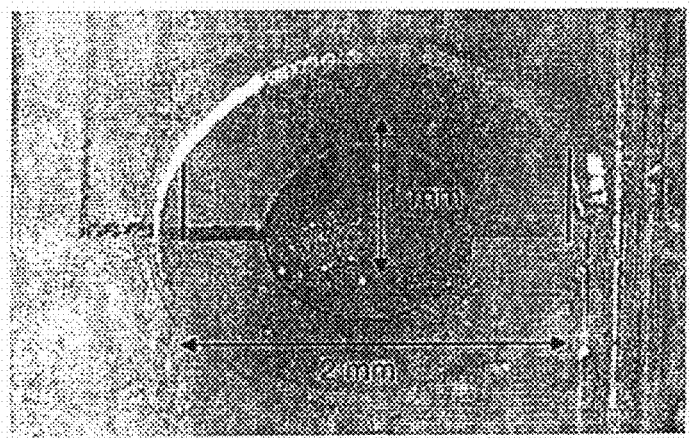
FIG. 1B is an optical picture of the fabricated quartz crystal resonator showing the etch pit and the gold electrode (Note: The optical image shows the opposite face of the resonator in comparison to the schematic illustration to highlight the etched surface). The diameter of the etched diaphragm was 2 mm and the diameter of the Au/Cr (100 nm/20 nm) electrode was 1 mm. The diaphragm was etched in a 1" AT-cut quartz disc, 110 µm thick, obtained from Boston Piezo-Optics Inc. The final thickness of the diaphragm realized was ~34 µm.
Figure 2:
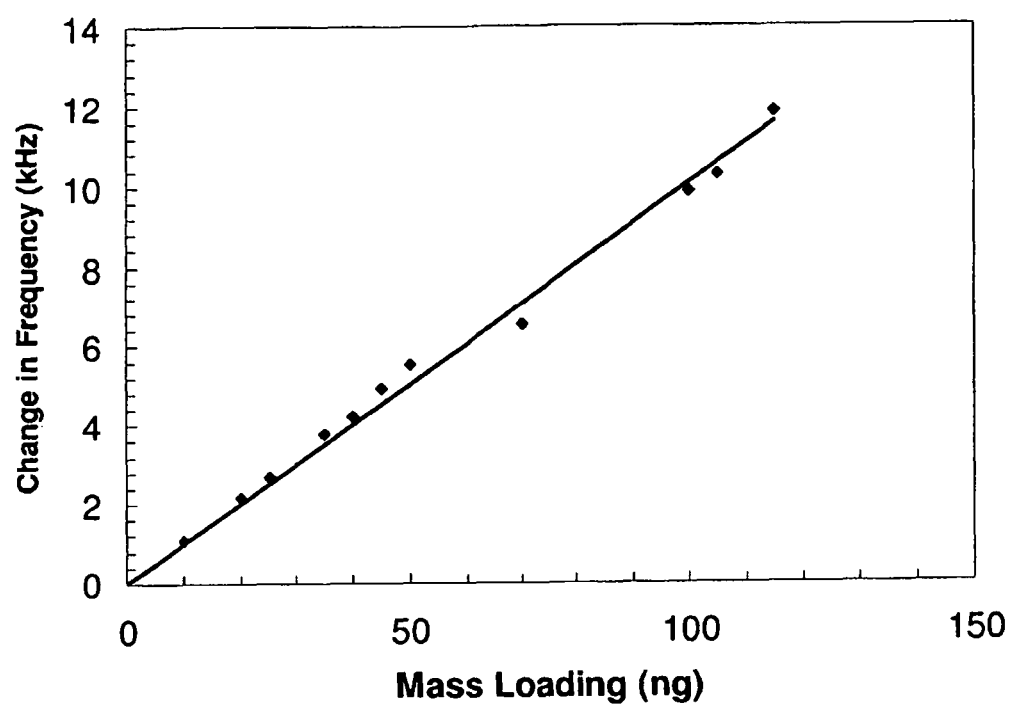
FIG. 2 is a mass calibration curve of the 90 µm thick quartz resonator obtained by deposition of glucose. The quartz resonator has a 1 mm diameter electrode on a 2 mm diameter etched area. The diaphragm was etched on a 1" diameter 175 micron thick AT-cut quartz disc. Mass sensitivity experiments were conducted by loading the electrode with 0.5 µliter drops of 0.1 mM solution of glucose using a syringe pump. The dispensed volume was allowed to evaporate, leaving behind the glucose and the frequency shift was then recorded. Mass sensitivity of 97 Hz/ng (theoretical value=101 Hz/ng) was obtained for this resonator thickness and electrode area.

Using an inductively coupled plasma etcher and $SF_6$ gas chemistry, we were able to etch AT-cut quartz at an etch rate of ~0.2 µm/min using a 10 µm thick, patterned, nickel overlayer as the mask. The rms roughness of the etched surface was found to be ~1 nm (peak to valley roughness of 2.5 nm) after an etch depth of ~70 µm while, the rms roughness of the as polished side of the quartz crystal of ~8 nm (peak to valley roughness of 60 nm). We etched quartz resonators of two different thicknesses 90 µm and 34 µm, each with a diameter of 2 mm and an electrode diameter of 1 mm as shown in FIGS. 1A and 1B. As shown in FIG. 1A, there is a micromachined quartz resonator 10 on a substrate 12 having an etched diaphragm 14 with an electrode 16. For the as fabricated resonators, Q-factors of ~28000 for the third mode for the 90 µm thick resonator and ~7000 for the fundamental mode for the 34 μm thick resonator at room temperature and in vacuum ($6.5 \times 10^{-4}$ mbar) were observed. Mass sensitivity calibration in the nanogram range (FIG. 2) was performed on the 90 μm thick resonator using a dilute aqueous glucose solution that was allowed to evaporate. The linearity of the calibration data is consistent with a uniform mass loading on the resonator. However, this technique cannot be used for picogram sensitivity measurements due to the variability in aerial density of the deposited glucose.

Single-walled carbon nanotube overlayer was used for performing the picogram sensitivity experiments on the 34 μm thick resonator. A solution of debundled SWNTs (a mixture of ~1/3 metallic and ~2/3 semiconducting nanotubes procured from Carbolux Inc.) in NMP (N-methyl-2-pyrrolidinone) was prepared along the route described in detail recently[11]. The density of the solution was 10 mg/ml (mass of SWNT/volume of NMP). AFM measurements were made to determine the fraction (~80-90%) of tubes appearing as single isolated tubes on the substrate. The SWNTs were typically ~1.4 nm in diameter and ~800 nm in length. The same solution was then sprayed in controlled bursts over the QCM surface using an air brush. The NMP solvent was allowed to evaporate, leaving behind a randomly oriented, uniform deposit of SWNTs on the gold electrode pattern of the QCM.

The resonator was connected to a HP4294A impedance analyzer and the in-phase and quadrature impedance of the resonator was monitored as the frequency was scanned. At resonance, the phase of the resonator as numerically fitted with a Lorentzian lineshape. A program in Mathematica® was written to fit the observed data to a Lorentzian function which included compensation for any superposed asymmetries in the phase curve. From the best fit to the data, the center frequency and the Q-factor were extracted numerically. The resonance frequency and the Q-factor were measured before and after coating the surface with the nanotubes, and measured in the laboratory atmosphere and in vacuum ($6.5 \times 10^{-4}$ mbar).

For the as-fabricated resonator, the resonance frequency and the Q-factor for the first mode were found, respectively, to be 48.535731 MHz and 6986.3 in air. Upon coating the micromachined surface with a layer of SWNTs, they decreased by $\Delta f = 3625.4$ Hz and $\Delta Q = 580.3$. This result suggests that after the visible evaporation of the solvent, the randomly oriented matt of nanotubes film acts as a rigid mass layer with dissipation. Using Sauerbrey mass sensitivity eq. 1 for the 34 μm resonator, the decrease in the resonance frequency upon the addition of nanotubes indicates a mass loading of 5.3387 ng after the initial evaporation of the NMP solvent. The Q-factor, as expected, decreased from the original value of the uncoated device when measured in air.

Figure 3:
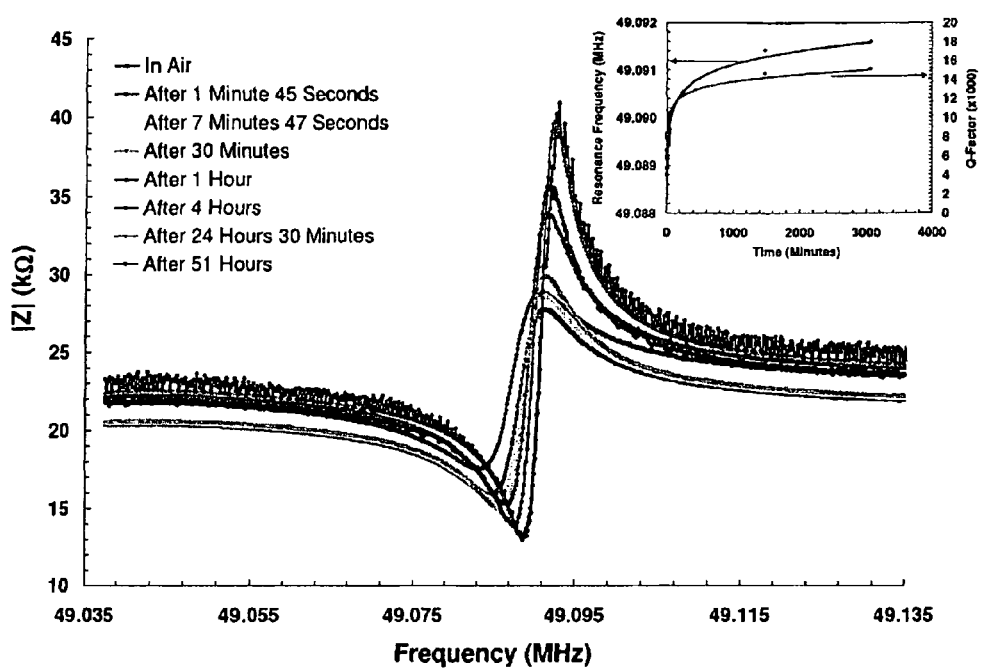
FIG. 3 illustrates resonance curves over extended period of time showing an increase in the resonance frequency and the quality factor due to desorption of trapped and physisorbed molecules from the carbon nanotubes on the resonator surface. Inset shows the evolution of resonance frequency and quality factor over time in vacuum. The curves show a characteristic logarithmic behavior which is consistent with the view that desorption of the molecules from the nanotubes is probabilistic. The lines are logarithmic fits to the data and are intended as a guide to the eye.

However, when the nanotube-coated device was left in the vacuum chamber for an extended period of time, a small increase in the resonance frequency was observed. Even more surprising was the observation of an increase in the Q-factor[12]. After additional spraying of nanotubes on the other side (manufacturer polished surface) of the resonator, the measurements were once again repeated in vacuum, the Q-factor was again found to increase. In fact, a net increase in the Q-factor of more than 100% (Q=15141.8) was observed upon leaving it in a vacuum of $6.5 \times 10^{-4}$ mbar for ~51 hours. FIG. 3 shows the evolution of the resonance curves of the SWNT-coated resonator in vacuum due to the slow desorption of the gases from the SWNTs. Inset in FIG. 3 shows the time evolution of the resonance frequency and the Q-factor for the 34 μm thick resonator. This resonator is expected to be 7 times more sensitive than the 90 μm thick resonator for which the mass calibration (FIG. 2) is shown. Thus after 51 hours of desorption the observed frequency increase of ~3.662 kHz (FIG. 3 inset) corresponds to a mass change of ~5.3982 ng.

Carbon nanotubes are known to adsorb a variety of molecules on their surfaces and in their interiors. Even after all the macroscopically observable NMP has evaporated off the surface of the resonators the "remaining mass" on the resonator surface is likely to include the mass of the nanotubes and some mass from the NMP solution and other molecules that are either physisorbed or trapped within the nanotubes. This can easily account for the large change in the desorbed mass reported above. When the same nanotube coated resonator was exposed back to air, the measured resonance frequency after a few minutes in air decreased by $\Delta f = 750$ Hz (relative to the frequency after 51 hours in vacuum) corresponding to a mass change of ~1 ng. It must be emphasized that part of this response is also from the damping induced in the bare quartz resonator from the surrounding air. In fact, ~600 Hz frequency decrease was observed on the 34 μm thick bare resonator between vacuum and air ambients. Due to the fact the nanotubes are uniformly dispersed over the surface of the resonator, a frequency resolution of 1.0-0.1 Hz, allows for a direct mass sensitivity measurement (unloading) in the 1 pg-100 fg range.

Intuitively, it can be expected that films deposited on resonators, will add a dissipation channel, i.e., decrease the Q-factor of the unloaded device. However, as seen in Table 1, the Q-factor for the first mode of the 34 μm thick quartz resonator with SWNT coatings increases in vacuum. Another important observation is that the net increase in the Q-factor of the resonator was more pronounced when the SWNTs were deposited on the rougher surface.

TABLE 1

The quality factor of a 34 μm thick micromachined quartz resonator.

| | Q-Factor of | | |
|---|---|---|---|
| Ambient | As Fabricated Resonator | After SWNT deposition on Micromachined Surface | After SWNT deposition on the manufacturer polished surface |
| Air | 6986.3 | 6406.0 | 6594.2 |
| Vacuum* (After 5 min) | 7353.9 | 6998.2 | 8188.6 |
| Vacuum* (after 4.5 hours in vacuum) | 7353.9 | 7939.2 | 12633.4[†] |

*At a vacuum of ~$6.5 \times 10^{-4}$ mbar.
[†]The Q-factor was measured after 4 hours in this case. The Q-factor of the resonator eventually increased to 15141.8 after 51 hours in vacuum.

Our observation of the increase in the Q-factor of a SWNT-coated resonator in vacuum can be explained by the desorption; of gas molecules from the nanotube surfaces. Two mechanisms for gas-induced energy dissipation present themselves: (i) nanotubes slipping over the each other (or the resonator surface) in the presence of adsorbed molecules, and (ii) conversion of the acoustical energy into kinetic energy of the gas trapped in the SWNTs. Further studies need to be carried out to elucidate the dominant mechanism.

To understand the dependence of the Q-factor on surface roughness, it is important to note that the scattering of the surface acoustic waves into bulk waves and other guided waves is known to increase as the magnitude of the surface roughness increases[13,14]. The converse must be also true, in that some of the energy from the bulk wave is transferred into surface waves due to the random surface roughness of the quartz crystal. However, unlike the bulk shear mode waves which are essentially confined due to energy trapping, the surface waves are unconfined, and they will propagate away along the surface of the quartz crystal dissipating their energy. Even though the SWNT film is held on the surface by the van der Waals force, our data is consistent with the view that the film acts to stiffen the surface and suppresses the coupling of energy into surface acoustic modes. Recently strong attenuation of the surface acoustic waves (SAW) in the 30-100 MHz range by SWNTs has been observed and attributed to the acoustoelectronic interaction of the SAW and charge carriers in the nanotubes[15]. Since the higher rms roughness on the manufacturer polished surface is expected to result in a greater coupling of the bulk waves to the surface waves on that surface which in turn are suppressed by the nanotube coating, a higher Q-factor improvement is seen for rougher surfaces.

Figure 4:
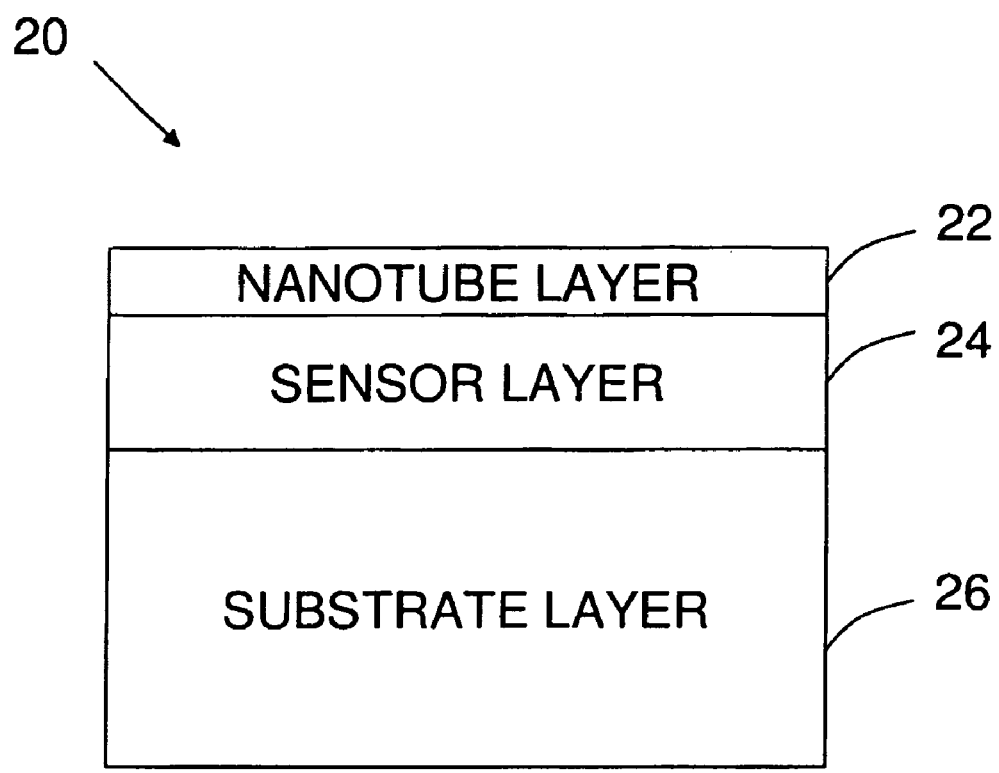
FIG. 4 is a block diagram showing different layers of one embodiment of a sensing device of the present invention.

FIG. 4 illustrates one embodiment of the present invention. FIG. 4 illustrates a sensing device 20 having a substrate layer 26, a sensor layer 24, and a nanotube layer 22. The nanotube layer 22 is used to assist in controlling frequency stability of quality factor of the sensing device 20. Where the sensor layer 24 includes a resonator, the adding of the nanotube layer 22 can provide for tuning the frequency of the resonator a desired level, preferably increasing the frequency stability of the resonator. The sensor layer 24 can include one or more sensors of various types. The sensor shown can be a conducting and non-conducting regions sensor, a SAW sensor, a Quartz Crystal Microbalance sensor, a conductive composite sensor, a piezoelectric sensor, or a sensor based on a cantilever or bridge. Where the sensor is based on a cantilever or bridge, the cantilever or bridge may be constructing using techniques such as, but not limited to, micromachining, chemical vapor deposition, physical vapor deposition, and plasma enhanced deposition. The sensor can include a resonator such as a shear mode resonator.

The nanotube layer 22 may be a film layer. The nanotube layer 22 can be deposited using a spray on, spin on, vacuum deposition, or in situ growth technique. The nanotube layer 22 may be comprised of a number of different types of materials including carbon, a semiconductor material, a polymer material, an organic material, or a combination of such materials.

The nanotube layer 22 may be used as a functionalization layer. Where used in such a manner, the functionalization layer is adapted for use in an application such as a gas sensing application, a virus detection application, a DNA sequencing application, an artificial olfactory unit application, a hydrogen storage element application, or a biochemical application.

Also, the nanotube layer may be added on one face of the sensor and another face may be coated with a functionalization layer. In this case, the functionalization layer may be a SAM or a polymer. Instead, the nanotube layer may be added to one face of the sensor and another face may be coated with nanowires, nanofibers, thin films, or other nanostructures. Where nanowires or nanofibers are used, they may be made from materials such as polymers, semiconductors, or carbon.

Alternatively, the substrate layer 26 may be formed from a single substrate or multiple substrates. Where multiple substrates are used, the multiple substrates serve as functional elements of the sensor.

The sensor may be adapted for use to detect binding between a first and second member of a recognition pair. The recognition pair may be an antigen-antibody, ligand-receptor, sugar-lectin, biotin-avidin, enzyme-substrate, oligonucleotide-oligonucleotide with a complementary sequence, oligonucleotide-protein, or oligonucleotide-cell.

Figure 5:
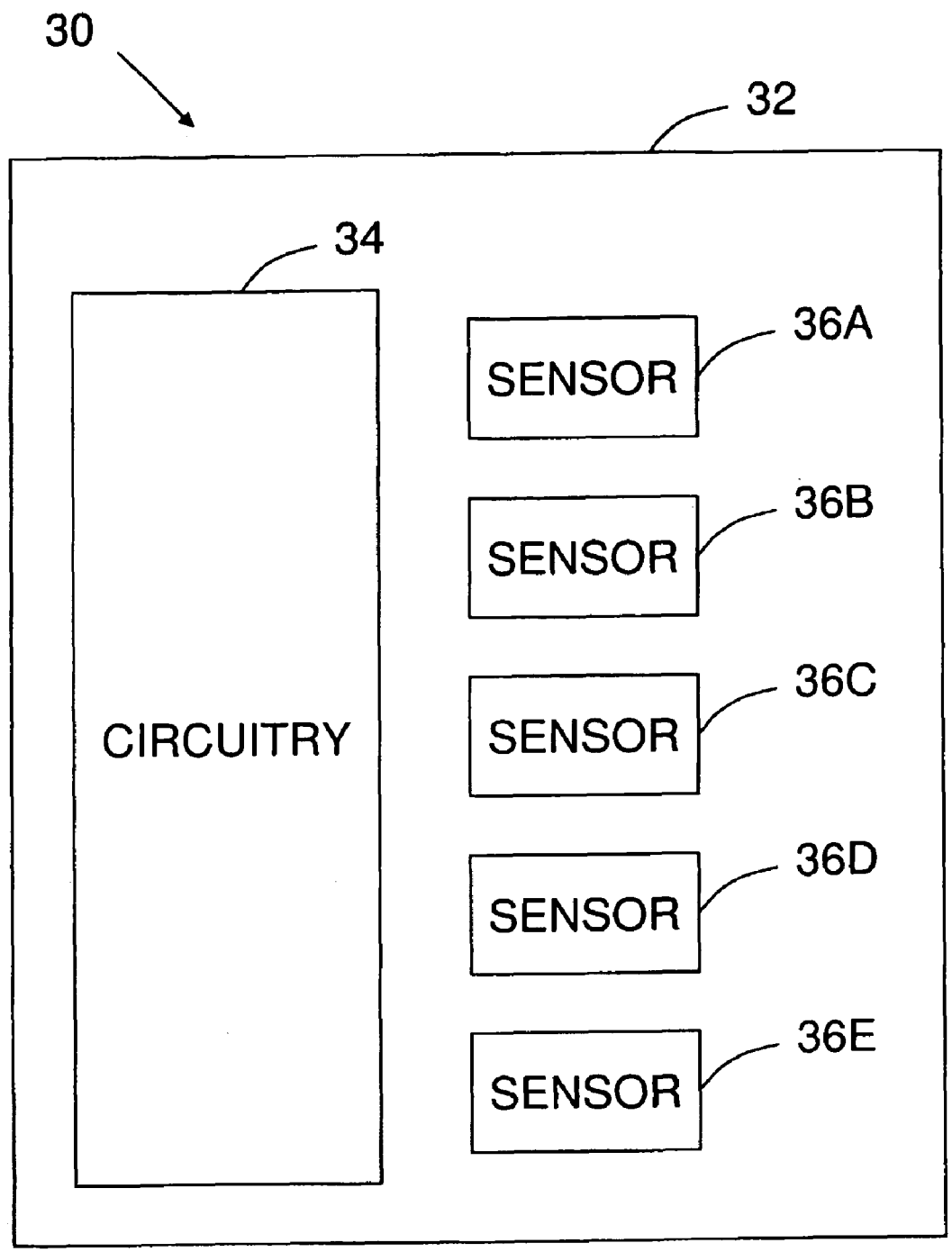
FIG. 5 is a block diagram showing an array of sensors according to one embodiment of the present invention.

FIG. 5 illustrates one embodiment of a sensing device of the present invention. A sensing device 30 has a housing 32. Within the housing, on the same substrate or otherwise, are a plurality of sensors 36A, 36B, 36C, 36D, 36E, which are operatively connected to circuitry 34. Each of the sensors 36A, 36B, 36C, 36D, 36E includes a layer of nanotubes. The circuitry 34 can include automatic gain controllers, amplitude controllers, phase controllers, temperature controllers, oscillators, input ports for subjecting the sensors to an input signal, and output-ports for reading the response of the sensors. The circuitry may also include interface circuitry for connection to other devices, including, for example, a computer. A preconcentrator may also be enclosed within the housing 32. The housing 32 may be adapted to function as a radiation shield, an electromagnetic radiation shield, or may be adapted to control the ambient temperature of the sensors.

The sensing device 30 is preferably portable and handheld. Each sensor can be integrated with thermopiles. Each sensor can be configured for various uses, such as a pressure sensor, a mass sensor, or a temperature sensor.

One skilled in the art having the benefit of this disclosure will appreciate the broad scope of the invention and the numerous variations of the invention. For example, the present invention contemplates numerous variations in the type of sensors used, the techniques used to make the sensing device, the type of nanotubes used, and other variations.

REFERENCES

[1] V. N. Hung, T. Abe, P. N. Minh, and M. Esashi, Applied Physics Letters 81, 5069-5071 (2002).

[2] J. Rabe, S. Büttgenbach, J. Schröder, and P. Hauptmann, IEEE Sensors Journal 3, 361-368 (2003).

[3] A. Janshoff, H-J. Galla, and C. Steinem, Angewandte Chemie International Edition 39, 4004-4032 (2000).

[4] C. Hagleitner, A. Hierlemann, D. Lange, A. Kummer, N. Kerness, O. Brand, and H. Baltes, Nature 414, 293-296 (2001).

[5] B. Ilic, H. G. Craighead, S. Krylov, W. Senaratne, C. Ober, and P. Neuzil, Journal of Applied Physics 95, 3694-3703 (2004).

[6] G. Sauerbrey, Zeitschrift fur Physik 155, 206-222 (1959).

[7] For AT-Cut Quartz, $m_q=2.947\times10^{10}$ N m-2 and $r_q=2.648\times10^3$ kg·m-3

[8] B. A. Martin, and H. E. Hager, Journal of Applied Physics 65, 2630-2635 (1989).

[9] B. Borovsky, B. L. Mason, and J. Krim, Journal of Applied Physics 88, 4017-4021 (2000).

[10] A. C. Hillier, and M. D. Ward, Analytical Chemistry 64, 2539-2554 (1992).

[11] C. A. Furtado, U. J. Kim, H. R. Gutierrez, L. Pan, E. C. Dickey, and P. C. Eklund, Journal of American Chemical Society Accepted for Publication (2004).

[12] J. R. Gladden, Ph.D. Thesis, Ph.D. Thesis, The Pennsylvania State University, 2003.

[13] A. G. Eguiluz, and A. A. Maradudin, Physical Review B 28, 728-747 (1983).

[14] A. P. Mayer, and M. Lelher, Waves in Random Media 4, 321-335 (1994).

[15] D. Ciplys, S. Rumyantsev, M. S. Shur, R. Vajtai, B. Wei, P. Ajayan, R. Gaska, and R. Rimeika, MRS Symposium 750, 211-216 (2003).

What is claimed is:

1. A method for increasing the quality factor of at least one sensor comprising:
   adding a layer of nanotubes to the at least one sensor to thereby increase the quality factor of the at least one sensor and form a nanotube-coated device;
   placing the nanotube-coated device in a vacuum chamber for a period of time sufficient to further increase the quality factor of the at least one sensor.

2. The method of claim 1 wherein the at least one sensor is a selected from a group consisting of a conducting and non-conducting regions sensor, a SAW sensor, a quartz crystal microbalance sensor, a conductive composite sensor, a piezoelectric sensor, and a sensor based on a cantilever or bridge.

3. The method of claim 1 wherein the at least one sensor comprises a resonator.

4. The method of claim 3 further comprising making a direct mass sensitivity measurement of the resonator.

5. The method of claim 3 wherein the resonator comprises a quartz crystal.

6. The method of claim 1 wherein the step of adding is performed by a technique selected from the group consisting of spray on, spin on, vacuum deposition, and in situ growth.

7. The method of claim 1 wherein the nanotubes are carbon nanotubes.

8. The method of claim 7 wherein the layer of carbon nanotubes is a functionalization layer.

9. The method of claim 8 wherein the functionalization layer is adapted for use in an application selected from the set consisting of a gas sensing application, a virus detection application, a DNA sequencing application, an artificial olfactory unit application, a hydrogen storage element application, and a biochemical application.

10. A sensing device comprising: a nanocoated device formed by adding a layer of single wall nanotubes to a quartz crystal sensor to thereby increase quality factor of the sensor and placing the nanotube-coated device in a vacuum chamber for a period of time sufficient to further increase the quality factor of the sensor.

11. The sensing device of claim 10 wherein the quartz crystal sensor is a microbalance sensor.

* * * * *

UNITED STATES PATENT AND TRADEMARK OFFICE
CERTIFICATE OF CORRECTION

| | | |
|---|---|---|
| PATENT NO. | : 7,814,776 B2 | Page 1 of 1 |
| APPLICATION NO. | : 11/719120 | |
| DATED | : October 19, 2010 | |
| INVENTOR(S) | : Peter C. Eklund et al. | |

It is certified that error appears in the above-identified patent and that said Letters Patent is hereby corrected as shown below:

In the Specification

Col. 1, Line 3, Before Priority Statement Insert the following paragraph:
--GRANT REFERENCE
This invention was made with government support under Grant No. MCE0096097, awarded by the National Science Foundation. The Government has certain rights in the invention.--

Signed and Sealed this
Eleventh Day of November, 2014

Michelle K. Lee
*Deputy Director of the United States Patent and Trademark Office*